(12) United States Patent
Liu et al.

(10) Patent No.: US 11,354,561 B2
(45) Date of Patent: Jun. 7, 2022

(54) SYSTEM AND METHOD FOR ON-LINE ANALYSIS OF STRUCTURE OF DRIED SHREDDED TOBACCO

(71) Applicant: Zhangjiakou Cigarette Factory Co., Ltd, Zhangjiakou (CN)

(72) Inventors: Bo Liu, Zhangjiakou (CN); Zijuan Li, Zhangjiakou (CN); Jia Sun, Zhangjiakou (CN); Hang Yin, Zhangjiakou (CN); Yang Gao, Zhangjiakou (CN); Liyuan Zhao, Zhangjiakou (CN); Wangchang Miao, Zhangjiakou (CN); Jiaojiao Chen, Zhangjiakou (CN); Zixian Feng, Zhangjiakou (CN); Zheng Zhou, Zhangjiakou (CN); Xiaohui Jia, Zhangjiakou (CN); Chao Li, Zhangjiakou (CN)

(73) Assignee: Zhangjiakou Cigarette Factory Co., Ltd, Zhangjiakou (CN)

( * ) Notice: Subject to any disclaimer, the term of this patent is extended or adjusted under 35 U.S.C. 154(b) by 0 days.

(21) Appl. No.: 17/471,120

(22) Filed: Sep. 9, 2021

(65) Prior Publication Data

US 2022/0012559 A1 Jan. 13, 2022

(30) Foreign Application Priority Data

Jul. 10, 2020 (CN) .......................... 202010662314.3

(51) Int. Cl.
*G06N 3/02* (2006.01)
*A24B 7/14* (2006.01)
(Continued)

(52) U.S. Cl.
CPC ................. *G06N 3/02* (2013.01); *A24B 7/14* (2013.01); *G01N 21/84* (2013.01);
(Continued)

(58) Field of Classification Search
None
See application file for complete search history.

(56) References Cited

U.S. PATENT DOCUMENTS 2,949,919 A * 8/1960 Johnson .................... A24B 1/08
131/327
4,497,330 A * 2/1985 Banyasz ............... A24B 15/403
131/296
(Continued)

FOREIGN PATENT DOCUMENTS

| CN | 106324125 | * | 1/2017 |
| CN | 106770303 A | | 5/2017 |

(Continued)

OTHER PUBLICATIONS

Automated Tobacco Grading Using Image Processing Techniques and a Convolutional Neural Network; Marzan et al Dec. 2019 (Year: 2019).*
(Continued)

*Primary Examiner* — Nancy Bitar
(74) *Attorney, Agent, or Firm* — Bayramoglu Law Offices LLC

(57) ABSTRACT

A system and a method for on-line analysis of a structure of dried shredded tobacco are provided. The system includes a shredded tobacco structure on-line analysis module, a shredded tobacco filling capacity prediction model module, and an early-warning module. The shredded tobacco structure on-line analysis module includes a sample extraction unit, a sample analysis unit and a shredded tobacco filling capacity data acquisition unit. The shredded tobacco filling capacity prediction model module includes a model parameter screening unit and a model construction unit. An early-warning threshold is provided in the early-warning module, and when a deviation of a predicted shredded tobacco filling capacity from a standard value exceeds the early-warning (Continued)

threshold, an alarm is given. The new system is an intelligent system with functions of shredded tobacco structure analysis, shredded tobacco filling capacity prediction, and abnormality early-warning determination and analysis.

8 Claims, 1 Drawing Sheet

(51) Int. Cl.
  *G01N 21/84*   (2006.01)
  *G01N 33/00*   (2006.01)
  *G06T 7/00*   (2017.01)
  *G06T 7/60*   (2017.01)

(52) U.S. Cl.
  CPC ....... *G01N 33/0098* (2013.01); *G06T 7/0004* (2013.01); *G06T 7/60* (2013.01); *G01N 2021/8466* (2013.01); *G06T 2207/30108* (2013.01)

(56) References Cited

U.S. PATENT DOCUMENTS

| | | | | |
|---|---|---|---|---|
| 4,607,646 A | * | 8/1986 | Lilly, Jr. ................ | A24B 15/28 |
| | | | | 131/309 |
| 5,746,225 A | * | 5/1998 | Okumoto ............. | A24C 5/1871 |
| | | | | 131/281 |

FOREIGN PATENT DOCUMENTS

| | | | |
|---|---|---|---|
| CN | 106932298 A | | 7/2017 |
| CN | 107153104 A | | 9/2017 |
| CN | 109239082 A | | 1/2019 |
| CN | 109259291 A | | 1/2019 |
| CN | 109740293 A | | 5/2019 |
| CN | 109984375 A | | 7/2019 |
| CN | 110763601 A | | 2/2020 |
| CN | 111887460 | * | 11/2020 |
| JP | WO2019/026201 | * | 2/2019 |
| WO | 8400284 A1 | | 2/1984 |

OTHER PUBLICATIONS

Development of Machine Learning Models for Prediction of Smoking Cessation Outcome; Cheng-Chien Lai 1; Feb. 2021 (Year: 2021).*
YC/T178-2003, Measurement of whole cut rate and broken cut rate, China National Standards GB Standard English Title: Measurement of whole cut rate and broken cut rate, 2003, State Tobacco Monopoly Adminstration.
Lu Yuhao, et al., Study on the Forecasting Model of Cut Tobacco Filling Value Based on the Neural Network, Chinese Tobacco Science, 2016, pp. 82-86, 37(5).
He Banghua, et al., Physical Quality of Tobacco Production and Primary Processing Neural Network Model and Its Evaluation, Journal of Yunnan Agricultural University (Natural Science), 2016, pp. 874-879, 31(5).
Xiaodu Chen, et al., Method for controlling the moisture contellt of the loose regained outlet of cigarette shreds based on Elman neural network, 2016, pp. 118-119, 136, Anhui Agri. Sci. Bull.

* cited by examiner

SYSTEM AND METHOD FOR ON-LINE ANALYSIS OF STRUCTURE OF DRIED SHREDDED TOBACCO

CROSS REFERENCE TO THE RELATED APPLICATIONS

This application is based upon and claims priority to Chinese Patent Application No. 202010662314.3, filed on Jul. 10, 2020 the entire contents of which are incorporated herein by reference.

TECHNICAL FIELD

The present invention relates to the tobacco industry, specifically to the link of shredded tobacco production, and more particularly to a system and method for on-line analysis of a structure of dried shredded tobacco.

BACKGROUND

In the tobacco production process, shredded tobacco production is a very important step. In this step, tobacco leaves are made into qualified shredded tobacco through various processing procedures based on the physical and chemical properties of the tobacco leaves.

A shredded tobacco structure directly affects a shredded tobacco filling capacity and a rolling quality. The shredded tobacco is composed of medium-long shredded tobacco, short shredded tobacco, and broken shredded tobacco, and the structure thereof directly affects the physical and chemical indexes of finished cigarettes.

The shredded tobacco filling capacity is a key index when the shredded tobacco is used for rolling, which refers to a volume of the shredded tobacco maintained after undergoing a specified pressure for a specified time period. The shredded tobacco filling capacity plays a leading role in the weight, consumption reduction, burning capacity, scorch reduction, and other indexes of cigarettes.

At present, a shredded tobacco structure is determined by multi-layer vibratory screening, and after the screening, shredded tobacco is weighed. According to the requirements of YC/T178-2003 of *Method for Measuring Whole Shredded Tobacco Rate and Broken Shredded Tobacco Rate*, this method has high requirements on instruments and requires five screen mesh layers, and operators are required to operate and record data according to rules. During analysis, the data is relatively simple and only involves a weight of shredded tobacco at each screen mesh layer, and thus the analyzable content is limited.

Chinese patent application CN110763601A discloses a shredded tobacco screening instrument and a method for determining the distribution of a shredded tobacco structure. The shredded tobacco screening instrument includes seven screen mesh layers, and the mesh diameters of the first screen mesh layer to the seventh screen mesh layer decrease from top to bottom. Specifically, mesh diameters of the fourth, fifth and sixth screen mesh layers are set according to preset determination conditions. The method includes: screening a shredded tobacco sample for three times to obtain first screening data, second screening data and third screening data; obtaining mass distribution interval data of the to-be-determined shredded tobacco sample based on the first screening data, the second screening data and the third screening data; and obtaining the distribution of the shredded tobacco structure of the to-be-determined shredded tobacco sample based on the mass distribution interval data and a cumulative distribution function of the shredded tobacco.

Chinese patent application CN106770303A discloses a method for characterizing a shredded tobacco structure of a cigarette based on image analysis, which belongs to the technical field of characterization methods of shredded tobacco structures. The method includes the following: extracting a small amount of shredded tobacco from a cigarette, spreading the shredded tobacco, and photographing; using a processing software to extract shredded tobacco number information and single-shredded tobacco length information in an image, and extracting plotting scale information in the image; and using the plotting scale to convert the shredded tobacco length information in the image into a shredded tobacco length. According to the above information, the following can be obtained: average length, minimum length, maximum length, and cumulative length of the sample shredded tobacco; average linear density of the shredded tobacco; quantitative structure of different shredded tobacco length segments; and frequency distribution and normal fitting curve for different shredded tobacco length segments. The method is simple and feasible, leads to diversified results, can finely characterize a shredded tobacco structure, and thus can be potentially used in the homogenization processing evaluation and the product quality difference analysis.

Chinese patent application CN109239082A discloses an on-line determination method of a shredded tobacco structural quality based on a machine vision technique, which includes the following steps: acquiring shredded tobacco images and relevant data of required batch production links, and constructing a target function library based on the relevant data; preprocessing the acquired shredded tobacco images to obtain effective shredded tobacco images, and enhancing the effective shredded tobacco images to obtain enhanced shredded tobacco images; extracting effective feature values in the enhanced shredded tobacco images, and constructing a shredded tobacco image feature library through the effective feature values; constructing a correlation model of shredded tobacco image features with the target function library; and obtaining a corresponding shredded tobacco structural quality index through the correlation model, and evaluating a shredded tobacco structural quality through the shredded tobacco quality evaluation index. In this method, the correlation model of the shredded tobacco image features with the target function library is constructed, which can overcome the shortcomings of a single shredded tobacco quality evaluation parameter; and shredded tobacco images are acquired in real time, which makes quality indexes in a shredded tobacco production process partially transparent and improves the evaluation accuracy.

SUMMARY

To overcome the above-mentioned problems, this application provides a system and method for on-line analysis of a structure of dried shredded tobacco.

The present invention is intended to use a machine vision technique to develop an intelligent shredded tobacco structure analysis system and method with functions of shredded tobacco structure analysis, shredded tobacco filling capacity prediction, and abnormality early-warning determination and analysis.

The present invention adopts the following technical solutions to solve the technical problems:

A system for on-line analysis of a structure of dried shredded tobacco includes:

a shredded tobacco structure on-line analysis module including a sample extraction unit, a sample analysis unit and a shredded tobacco filling capacity data acquisition unit, where the sample extraction unit is configured to extract 5 g±0.5 g of the dried shredded tobacco online and then acquire images of the dried shredded tobacco through an image acquisition device for detection by the sample analysis unit; the sample analysis unit is configured to automatically perform statistics on length data of the dried shredded tobacco through an image processing software and a data statistical software, and then perform interval grouping and storage on statistical data for a construction of a prediction model; and the shredded tobacco filling capacity data acquisition unit is configured to extract 10.0 g to 20.0 g of the dried shredded tobacco online and simultaneously put the dried shredded tobacco and the shredded tobacco extracted by the sample extraction unit into a shredded tobacco filling capacity detector for detection for the construction of the prediction model;

a shredded tobacco filling capacity prediction model module including a model parameter screening unit and a model construction unit, where the model construction unit constructs a first model and a second model through an artificial neural network (ANN) model, and performs a third construction through the ANN model based on an output parameter of the first model and an output parameter of the second model to obtain a third model; and the third model is a shredded tobacco filling capacity prediction model; and an early-warning module, where an early-warning threshold is provided in the early-warning module, and when a deviation of a predicted shredded tobacco filling capacity from a standard value exceeds the early-warning threshold, an alarm is given.

As an improvement of the above technical solutions, the early-warning module includes an abnormality analysis unit; and when the early-warning module gives the alarm:

the abnormality analysis unit compares the output parameter of the first model with a parameter actually acquired by a moisture meter; if the deviation is ≥10%, it is determined that a device parameter setting is abnormal and it is recommended to stop and check a device; and if the deviation is <10%, a prompt to check a tobacco shredding procedure before drying is given to determine whether an abnormal shredded tobacco filling capacity is caused by the tobacco shredding procedure.

As an improvement of the above technical solutions, the early-warning module gives the alarm when the deviation of the predicted shredded tobacco filling capacity from the standard value is ≥10%.

As an improvement of the above technical solutions, the image processing software is Image pro plus 6, and the data statistical software is Microsoft Excel.

As an improvement of the above technical solutions, the model parameter screening unit screens out model parameters of:

device parameters including a cylinder wall temperature of a thin-plate shredded tobacco dryer, an inlet moisture amount of the thin-plate shredded tobacco dryer, an outlet moisture amount of the thin-plate shredded tobacco dryer, a hot air temperature of the thin-plate shredded tobacco dryer, and an outlet temperature of the thin-plate shredded tobacco dryer; and shredded tobacco structure parameters including a long and short shredded tobacco rate, a broken shredded tobacco rate, and a measured shredded tobacco filling capacity.

As an improvement of the above technical solutions, the first model is a three-layer ANN model, and has three input values, two output values and two neurons; and the first model is configured to predict the outlet moisture amount of the thin-plate shredded tobacco dryer and the outlet temperature of the thin-plate shredded tobacco dryer.

As an improvement of the above technical solutions, the input values of the first model are the cylinder wall temperature of the thin-plate shredded tobacco dryer, the inlet moisture amount of the thin-plate shredded tobacco dryer, and the hot air temperature of the thin-plate shredded tobacco dryer; and the output values of the first model are the outlet moisture amount of the thin-plate shredded tobacco dryer and the outlet temperature of the thin-plate shredded tobacco dryer.

As an improvement of the above technical solutions, the second model is a three-layer ANN model, and has three input values, one output value and two neurons; and the second model is configured to predict the predicted shredded tobacco filling capacity.

As an improvement of the above technical solutions, the input values of the second model are the long and short shredded tobacco rate, the broken shredded tobacco rate, and the measured shredded tobacco filling capacity; and the output value of the second model is the predicted shredded tobacco filling capacity.

The present invention also provides a method for on-line analysis of a structure of dried shredded tobacco, and the method is applied to the system for on-line analysis of a structure of dried shredded tobacco described above and includes the following steps:

step 1: sample extraction:

extracting the 5 g±0.5 g of the dried shredded tobacco online, and acquiring images of the dried shredded tobacco through the image acquisition device for detection by the sample analysis unit;

step 2: sample analysis and statistics:

automatically performing statistics on the length data of the dried shredded tobacco through the image processing software and the data statistical software, and performing interval grouping and storage on the statistical data for the construction of the prediction model;

step 3: shredded tobacco filling capacity data acquisition:

extracting the 10.0 g to 20.0 g of the dried shredded tobacco online and simultaneously putting the dried shredded tobacco and the shredded tobacco extracted by the sample extraction unit into the shredded tobacco filling capacity detector for detection for the construction of the prediction model;

step 4: model parameter screening:

screening out, by a model parameter screening unit, model parameters of:

device parameters including a cylinder wall temperature of a thin-plate shredded tobacco dryer, an inlet moisture amount of the thin-plate shredded tobacco dryer, an outlet moisture amount of the thin-plate shredded tobacco dryer, a hot air temperature of the thin-plate shredded tobacco dryer, and an outlet temperature of the thin-plate shredded tobacco dryer; and shredded tobacco structure parameters including a long and short shredded tobacco rate, a broken shredded tobacco rate, and a measured shredded tobacco filling capacity;

step 5: model construction:

constructing the first model and the second model through the ANN model, and performing the third construction through the ANN model based on the output parameter of the first model and the output parameter of the second model to obtain the third model, where the third model is a final shredded tobacco filling capacity prediction model;

where, the first model is a model for predicting the outlet moisture amount of the thin-plate shredded tobacco dryer and the outlet temperature of the thin-plate shredded tobacco dryer; and the second model is a shredded tobacco filling capacity prediction model;

step 6: abnormality early-warning:

based on the models constructed in step 5, when a deviation of a predicted shredded tobacco filling capacity of the third model from a standard value exceeds an early-warning threshold, giving an alarm; and step 7: abnormality analysis:

when an early-warning module triggers an abnormality alarm, comparing, by an abnormality analysis unit, the output parameter of the first model with a parameter actually acquired by a moisture meter, where if the deviation is ≥10%, it is determined that a device parameter setting is abnormal and it is recommended to stop and check a device; and if the deviation is <10%, a prompt to check a tobacco shredding procedure before drying is given to determine whether an abnormal shredded tobacco filling capacity is caused by the tobacco shredding procedure.

The present invention has the following advantages:

In the present invention, an accurate predicted shredded tobacco filling capacity can be directly obtained through on-line sample extraction, model construction, and model prediction. The system of the present invention is an intelligent system with functions of shredded tobacco structure analysis, shredded tobacco filling capacity prediction, and abnormality early-warning determination and analysis.

In an application process, the present invention can save detection procedures and a large amount of detection time, achieve real-time detection of a device and shredded tobacco at the same time, determine an operating status of a device according to a prediction result, and automatically make abnormality determination and cause analysis, which is convenient for operators to discover production problems early, improves the production efficiency and product quality, and saves human resource costs.

BRIEF DESCRIPTION OF THE DRAWINGS

The present invention is described in more detail below with reference to the accompanying drawings and embodiments.

DETAILED DESCRIPTION OF THE EMBODIMENTS

The technical solutions in the embodiments of the present invention are clearly and completely described below with reference to the accompanying drawings in the embodiments of the present invention. Apparently, the described embodiments are merely a part rather than all of the embodiments of the present invention. All other embodiments obtained by a person of ordinary skill in the art based on the embodiments of the present invention without creative efforts shall fall within the protection scope of the present invention.

In the present invention, unless otherwise clearly specified and limited, terms "arrangement", "connection", and "fixation" should be understood in a board sense. For embodiment, the connection may be a fixed connection or a removable connection; may be a mechanical connection; and may be a direct connection or an indirect connection using an intermediate medium. Those of ordinary skill in the art may understand specific meanings of the above terms in the present invention based on a specific situation.

Embodiment 1

Figure 1:
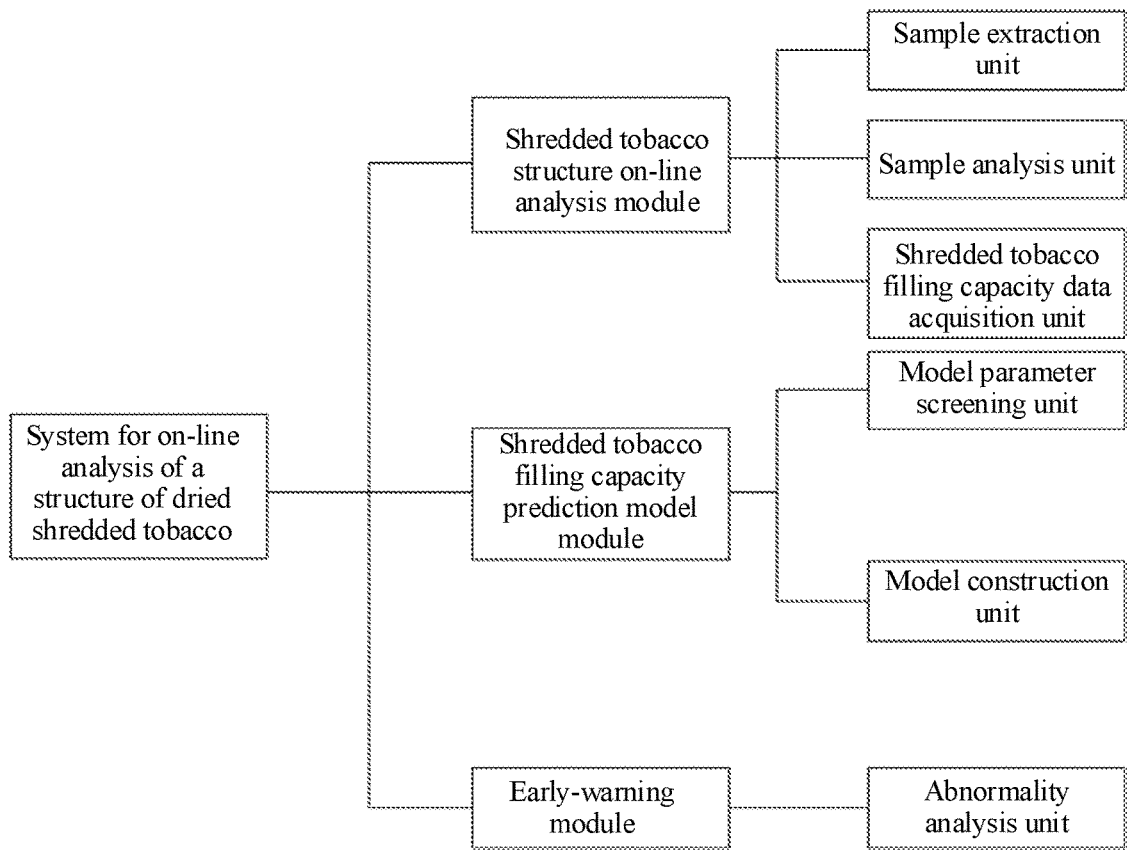
FIG. 1 is a system module diagram of the present invention.

As shown in FIG. 1, a system for on-line analysis of a structure of dried shredded tobacco is provided in this embodiment, including:

a shredded tobacco structure on-line analysis module including a sample extraction unit, a sample analysis unit and a shredded tobacco filling capacity data acquisition unit, where the sample extraction unit is configured to extract 5 g±0.5 g of dried shredded tobacco online and then acquire images of the dried shredded tobacco through an image acquisition device for detection by the sample analysis unit; the sample analysis unit is configured to automatically perform statistics on length data of the dried shredded tobacco through an image processing software and a data statistical software, and then perform interval grouping and storage on statistical data for a construction of a prediction model; and the shredded tobacco filling capacity data acquisition unit is configured to extract 10.0 g to 20.0 g of dried shredded tobacco online and simultaneously put the dried shredded tobacco and the shredded tobacco extracted by the sample extraction unit into a shredded tobacco filling capacity detector for detection for the construction of the prediction model;

a shredded tobacco filling capacity prediction model module including a model parameter screening unit and a model construction unit, where the model construction unit constructs a first model and a second model through an ANN model, and performs a third construction through the ANN model based on an output parameter of the first model and an output parameter of the second model to obtain a third model; and the third model is a shredded tobacco filling capacity prediction model; and an early-warning module, where an early-warning threshold is provided in the early-warning module, and when a deviation of a predicted shredded tobacco filling capacity from a standard value is ≥10%, the early-warning module gives an alarm.

Further, the early-warning module may include an abnormality analysis unit; and when the early-warning module gives the alarm:

the abnormality analysis unit compares the output parameter of the first model with a parameter actually acquired by a moisture meter; if the deviation is ≥10% (deviation= (measured value−predicted value)/predicted value, the early-warning threshold is adjustable), it is determined that a device parameter setting is abnormal and it is recommended to stop and check a device; and if the deviation is <10%, a prompt to check a tobacco shredding procedure before drying is given to determine whether an abnormal shredded tobacco filling capacity is caused by the tobacco shredding procedure.

In this embodiment, the image processing software is Image pro plus 6, and the data statistical software is Microsoft Excel.

Further, the model parameter screening unit may screen out model parameters of:

device parameters including a cylinder wall temperature of a thin-plate shredded tobacco dryer, an inlet moisture amount of the thin-plate shredded tobacco dryer, an outlet moisture amount of the thin-plate shredded tobacco dryer, a hot air temperature of the thin-plate shredded tobacco dryer, and an outlet temperature of the thin-plate shredded tobacco dryer; and shredded tobacco structure parameters including a long and short shredded tobacco rate, a broken shredded tobacco rate, and a measured shredded tobacco filling capacity.

In this embodiment:

The first model is a three-layer ANN model, and has three input values, two output values and two neurons; and the first model is configured to predict the outlet moisture amount of the thin-plate shredded tobacco dryer and the outlet temperature of the thin-plate shredded tobacco dryer. The first model predicts the outlet moisture amount and the outlet temperature of the thin-plate shredded tobacco dryer to avoid a time difference between an extracted sample and actual production data, which will result in inaccurate model predictions.

Specifically, the input values of the first model are the cylinder wall temperature of the thin-plate shredded tobacco dryer, the inlet moisture amount of the thin-plate shredded tobacco dryer, and the hot air temperature of the thin-plate shredded tobacco dryer; and the output values of the first model are the outlet moisture amount of the thin-plate shredded tobacco dryer and the outlet temperature of the thin-plate shredded tobacco dryer.

In this embodiment:

The second model is a three-layer ANN model, and has three input values, one output value and two neurons; and the second model is configured to predict the predicted shredded tobacco filling capacity, such that only the shredded tobacco structure analysis is required in the later application process to obtain accurate predicted shredded tobacco filling capacity data.

Specifically, the input values of the second model are the long and short shredded tobacco rate, the broken shredded tobacco rate, and the measured shredded tobacco filling capacity; and the output value of the second model is the predicted shredded tobacco filling capacity.

Figure 2:
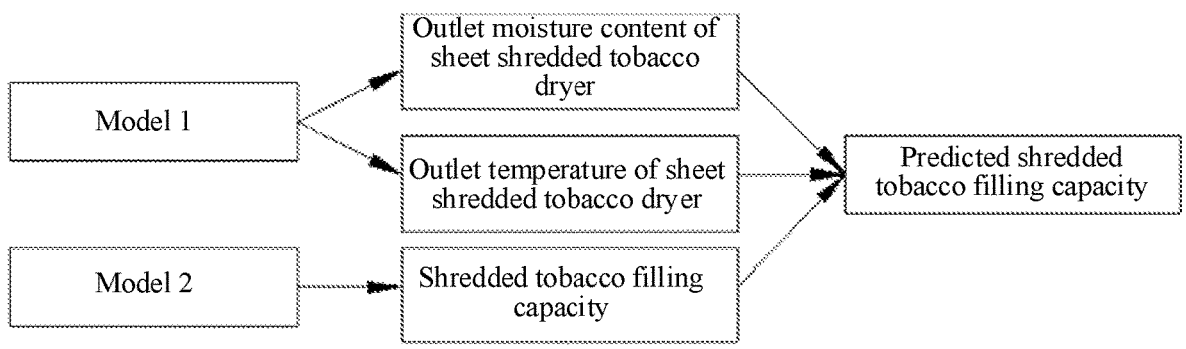
FIG. 2 is a schematic diagram of a constructing architecture of the prediction models of the present invention.

As shown in FIG. 2, the third model is obtained through a third construction of an ANN model based on the output values of the first model and the second model, and is configured to predict final predicted shredded tobacco filling capacity data. Output data of the first model participate in the calculation of a final value, which plays a role of data correction to avoid data errors caused by the adjustment of device parameters.

In this embodiment, an accurate predicted shredded tobacco filling capacity can be directly obtained through on-line sample extraction, model construction, and model prediction. The system of this embodiment is an intelligent system with functions of shredded tobacco structure real-time analysis, shredded tobacco filling capacity prediction, and abnormality early-warning determination and analysis.

Embodiment 2

A method for on-line analysis of a structure of dried shredded tobacco is provided, and the method is applied to the system for on-line analysis of a structure of dried shredded tobacco according to Embodiment 1 and includes the following steps:

Step 1. Sample extraction 5 g±0.5 g of dried shredded tobacco is extracted online and images of the dried shredded tobacco are acquired through an image acquisition device for detection by a sample analysis unit.

Step 2. Sample analysis and statistics

Length data of the dried shredded tobacco are automatically acquired through an image processing software and a data statistical software and interval grouping and storage are performed on statistical data for a construction of a prediction model.

Step 3. Shredded tobacco filling capacity data acquisition 10.0 g to 20.0 g of dried shredded tobacco is extracted online and the dried shredded tobacco is put together with the shredded tobacco extracted by a sample extraction unit into a shredded tobacco filling capacity detector for detection for the construction of the prediction model.

Step 4. Model parameter screening model parameters of are screened out by a model parameter screening unit:

device parameters including a cylinder wall temperature of a thin-plate shredded tobacco dryer, an inlet moisture amount of the thin-plate shredded tobacco dryer, an outlet moisture amount of the thin-plate shredded tobacco dryer, a hot air temperature of the thin-plate shredded tobacco dryer, and an outlet temperature of the thin-plate shredded tobacco dryer; and shredded tobacco structure parameters including a long and short shredded tobacco rate, a broken shredded tobacco rate, and a measured shredded tobacco filling capacity;

Step 5. Model construction

A first model and a second model is constructed through an ANN model, and a third construction is performed through the ANN model based on an output parameter of the first model and an output parameter of the second model to obtain a third model, where the third model is a final shredded tobacco filling capacity prediction model;

where, the first model is a model for predicting the outlet moisture amount of the thin-plate shredded tobacco dryer and the outlet temperature of the thin-plate shredded tobacco dryer; and output data of the first model participate in the final value prediction of the third model, which plays a role of data correction to avoid data errors caused by the adjustment of device parameters; and the second model is a shredded tobacco filling capacity prediction model (without correction), such that only the shredded tobacco structure analysis is required in the later application process to obtain accurate predicted shredded tobacco filling capacity data.

Step 6. Abnormality early-warning

Based on the models constructed in step 5, when a deviation of a predicted shredded tobacco filling capacity of the third model from a standard value exceeds an early-warning threshold ($\geq 10\%$), an alarm is given.

Step 7. Abnormality analysis

When an early-warning module triggers an abnormality alarm, an abnormality analysis unit compares the output parameter of the first model with a parameter actually acquired by a moisture meter; if the deviation is $\geq 10\%$, it is determined that a device parameter setting is abnormal and it is recommended to stop and check a device; and if the deviation is <10%, a prompt to check a tobacco shredding procedure before drying is given to determine whether an abnormal shredded tobacco filling capacity is caused by the tobacco shredding procedure.

Test Example

The system for on-line analysis of a structure of dried shredded tobacco in Embodiment 1 was used to subject shredded tobacco at an outlet of a second-stage thin-plate shredded tobacco dryer to structural analysis (prediction of shredded tobacco filling capacity). It was specified that sampling was conducted 10 times for each batch of shredded tobacco and a total of 5 batches were tested. Test results were as follows:

| Batch 1 | | | | | | | | | |
|---|---|---|---|---|---|---|---|---|---|
| 1 | 4.8 | 3 | 4.7 | 5 | 4.6 | 7 | 4.7 | 9 | 4.7 |
| 2 | 4.7 | 4 | 4.7 | 6 | 4.8 | 8 | 4.6 | 10 | 4.7 |
| Actual test result | | | | | 4.8 | | | | |

| Batch 2 | | | | | | | | | |
|---|---|---|---|---|---|---|---|---|---|
| 1 | 4.7 | 3 | 4.7 | 5 | 4.7 | 7 | 4.8 | 9 | 4.8 |
| 2 | 4.7 | 4 | 4.8 | 6 | 4.8 | 8 | 4.7 | 10 | 4.7 |
| Actual test result | | | | | 4.7 | | | | |

| Batch 3 | | | | | | | | | |
|---|---|---|---|---|---|---|---|---|---|
| 1 | 4.8 | 3 | 4.8 | 5 | 4.7 | 7 | 4.7 | 9 | 4.9 |
| 2 | 4.7 | 4 | 4.9 | 6 | 4.8 | 8 | 4.7 | 10 | 4.7 |
| Actual test result | | | | | 4.8 | | | | |

| Batch 4 | | | | | | | | | |
|---|---|---|---|---|---|---|---|---|---|
| 1 | 4.7 | 3 | 4.9 | 5 | 4.7 | 7 | 4.8 | 9 | 4.8 |
| 2 | 4.9 | 4 | 4.9 | 6 | 4.8 | 8 | 4.8 | 10 | 4.8 |
| Actual test result | | | | | 4.8 | | | | |

| Batch 5 | | | | | | | | | |
|---|---|---|---|---|---|---|---|---|---|
| 1 | 4.7 | 3 | 4.6 | 5 | 4.7 | 7 | 4.7 | 9 | 4.6 |
| 2 | 4.9 | 4 | 4.9 | 6 | 4.8 | 8 | 4.7 | 10 | 4.7 |
| Actual test result | | | | | 4.7 | | | | |

It can be seen that an accurate shredded tobacco filling capacity can be directly obtained through on-line sampling, structural analysis, and model prediction in the present invention.

Finally, it should be noted that the above description is only a preferred embodiment of the present invention and is not intended to limit the present invention. Although the present invention has been described in detail with reference to the foregoing embodiments, those skilled in the art can still modify the technical solutions described in the foregoing embodiments, or equivalently substitute some of the technical features of the embodiments. Any modifications, equivalent substitutions, improvements, and the like within the spirit and principle of the present invention should fall within the protection scope of the present invention.

What is claimed is:

1. A system for on-line analysis of a structure of dried shredded tobacco, comprising:
 a shredded tobacco structure on-line analysis module, wherein the shredded tobacco structure on-line analysis module comprises a sample extraction unit, a sample analysis unit and a shredded tobacco filling capacity data acquisition unit, wherein
  the sample extraction unit is configured to extract 5 g±0.5 g of the dried shredded tobacco online and then acquire images of the 5 g±0.5 g of the dried shredded tobacco through an image acquisition device for detection by the sample analysis unit;
  the sample analysis unit is configured to automatically perform statistics on length data of the 5 g±0.5 g of the dried shredded tobacco through an image processing software and a data statistical software to obtain statistical data, and then perform interval grouping and storage on the statistical data for a construction of a prediction model; and
  the shredded tobacco filling capacity data acquisition unit is configured to extract 10.0 g to 20.0 g of the dried shredded tobacco online and simultaneously put the 10.0 g to 20.0 g of the dried shredded tobacco and the 5 g±0.5 g of the dried shredded tobacco extracted by the sample extraction unit into a shredded tobacco filling capacity detector for detection for the construction of the prediction model;
 a shredded tobacco filling capacity prediction model module, wherein the shredded tobacco filling capacity prediction model module comprises a model parameter screening unit and a model construction unit, wherein
  the model construction unit constructs a first model and a second model through an artificial neural network (ANN) model, and performs a third construction through the ANN model based on an output parameter of the first model and an output parameter of the second model to obtain a third model; and
  the third model is a shredded tobacco filling capacity prediction model; and
 an early-warning module, wherein
  an early-warning threshold is provided in the early-warning module, and when a deviation of a predicted shredded tobacco filling capacity from a standard value exceeds the early-warning threshold, an alarm is given;
 wherein the model parameter screening unit screens out model parameters of:
  device parameters, wherein the device parameters comprise a cylinder wall temperature of a thin-plate shredded tobacco dryer, an inlet moisture amount of the thin-plate shredded tobacco dryer, an outlet moisture amount of the thin-plate shredded tobacco dryer, a hot air temperature of the thin-plate shredded tobacco dryer, and an outlet temperature of the thin-plate shredded tobacco dryer; and
  shredded tobacco structure parameters, wherein the shredded tobacco structure parameters comprise a long and short shredded tobacco rate, a broken shredded tobacco rate, and a measured shredded tobacco filling capacity;
 the first model is a three-layer ANN model, and has three input values, two output values and two neurons; the first model is configured to predict the outlet moisture amount of the thin-plate shredded tobacco dryer and the outlet temperature of the thin-plate shredded tobacco dryer; the three input values of the first model are the cylinder wall temperature of the thin-plate shredded tobacco dryer, the inlet moisture amount of the thin-plate shredded tobacco dryer, and the hot air temperature of the thin-plate shredded tobacco dryer; the two output values of the first model are the outlet moisture amount of the thin-plate shredded tobacco dryer and the outlet temperature of the thin-plate shredded tobacco dryer; and the second model is a three-layer ANN model, and has three input values, one output value and two neurons; the second model is configured to predict the predicted shredded tobacco filling capacity; the three input values of the second model are the long and short shredded tobacco rate, the broken shredded tobacco rate, and the measured shredded tobacco filling capacity; the one output value of the second model is the predicted shredded tobacco filling capacity.

2. The system according to claim 1, wherein
the early-warning module comprises an abnormality analysis unit; and
when the early-warning module gives the alarm, the abnormality analysis unit compares the output parameter of the first model with a parameter actually acquired by a moisture meter; wherein
when the deviation is ≥10%, a device parameter setting is abnormal, and a device is stopped and checked; and
when the deviation is <10%, a prompt to check a tobacco shredding procedure before drying is given to determine whether an abnormal shredded tobacco filling capacity is caused by the tobacco shredding procedure.

3. The system according to claim 1, wherein
the early-warning module gives the alarm when the deviation of the predicted shredded tobacco filling capacity from the standard value is ≥10%.

4. The system according to claim 1, wherein
the image processing software is Image pro plus 6, and the data statistical software is Microsoft Excel.

5. A method for on-line analysis of a structure of dried shredded tobacco, wherein the method is applied to the system according to claim 1 and comprises the following steps:
step 1: sample extraction:
extracting the 5 g±0.5 g of the dried shredded tobacco online, and acquiring images of the 5 g±0.5 g of the dried shredded tobacco through the image acquisition device for detection by the sample analysis unit;
step 2: sample analysis and statistics:
automatically performing statistics on the length data of the 5 g±0.5 g of the dried shredded tobacco through the image processing software and the data statistical software to obtain the statistical data, and performing interval grouping and storage on the statistical data for the construction of the prediction model;
step 3: shredded tobacco filling capacity data acquisition:
extracting the 10.0 g to 20.0 g of the dried shredded tobacco online and simultaneously putting the 10.0 g to 20.0 g of the dried shredded tobacco and the 5 g±0.5 g of the dried shredded tobacco extracted by the sample extraction unit into the shredded tobacco filling capacity detector for detection for the construction of the prediction model;
step 4: model parameter screening:
screening out, by a model parameter screening unit, model parameters of:
device parameters, wherein the device parameters comprise a cylinder wall temperature of a thin-plate shredded tobacco dryer, an inlet moisture amount of the thin-plate shredded tobacco dryer, an outlet moisture amount of the thin-plate shredded tobacco dryer, a hot air temperature of the thin-plate shredded tobacco dryer, and an outlet temperature of the thin-plate shredded tobacco dryer; and
shredded tobacco structure parameters, wherein the shredded tobacco structure parameters comprise a long and short shredded tobacco rate, a broken shredded tobacco rate, and a measured shredded tobacco filling capacity;
step 5: model construction:
constructing the first model and the second model through the ANN model, and performing the third construction through the ANN model based on the output parameter of the first model and the output parameter of the second model to obtain the third model, wherein the third model is a final shredded tobacco filling capacity prediction model;
wherein,
the first model is a model for predicting the outlet moisture amount of the thin-plate shredded tobacco dryer and the outlet temperature of the thin-plate shredded tobacco dryer; and
the second model is a shredded tobacco filling capacity prediction model;
step 6: abnormality early-warning:
based on the first model, the second model and the third model constructed in step 5, when the deviation of the predicted shredded tobacco filling capacity of the third model from the standard value exceeds the early-warning threshold, giving the alarm; and
step 7: abnormality analysis:
when an early-warning module triggers an abnormality alarm, comparing, by an abnormality analysis unit, the output parameter of the first model with a parameter actually acquired by a moisture meter, wherein
when the deviation is ≥10%, a device parameter setting is abnormal, and a device stopped and checked; and
when the deviation is <10%, a prompt to check a tobacco shredding procedure before drying is given to determine whether an abnormal shredded tobacco filling capacity is caused by the tobacco shredding procedure.

6. The method according to claim 5, wherein
the early-warning module comprises the abnormality analysis unit; and
when the early-warning module gives the alarm, the abnormality analysis unit compares the output parameter of the first model with the parameter actually acquired by the moisture meter; wherein
when the deviation is ≥10%, the device parameter setting is abnormal, and the device is stopped and checked; and
when the deviation is <10%, the prompt to check the tobacco shredding procedure before drying is given to determine whether the abnormal shredded tobacco filling capacity is caused by the tobacco shredding procedure.

7. The method according to claim 5, wherein
the early-warning module gives the alarm when the deviation of the predicted shredded tobacco filling capacity from the standard value is ≥10%.

8. The method according to claim 5, wherein the image processing software is Image pro plus 6, and the data statistical software is Microsoft Excel.

* * * * *